United States Patent
Goswami et al.

[11] Patent Number: 5,346,671
[45] Date of Patent: Sep. 13, 1994

[54] SPECIFIC AND REVERSIBLE CARBON MONOXIDE SENSOR

[75] Inventors: Kisholoy Goswami; Devinder P. S. Saini; Stanley M. Klainer, all of Henderson; Chuka H. Ejiofor, Las Vegas, all of Nev.

[73] Assignee: FCI - FiberChem, Inc., Las Vegas, Nev.

[21] Appl. No.: 22,324

[22] Filed: Feb. 25, 1993

Related U.S. Application Data

[63] Continuation-in-part of Ser. No. 9,066, Jan. 26, 1993.

[51] Int. Cl.$^5$ .................. G01N 31/00; G01N 33/00
[52] U.S. Cl. ......................... 422/86; 422/83; 436/134
[58] Field of Search .............. 422/83, 86, 98; 436/134, 169; 502/400, 406

[56] References Cited

U.S. PATENT DOCUMENTS

| | | | |
|---|---|---|---|
| 2,487,077 | 11/1949 | Shepherd | 436/134 |
| 4,043,934 | 8/1977 | Shuler et al. | 502/1 |
| 4,188,364 | 2/1980 | Gladden | 422/171 |
| 4,224,280 | 9/1980 | Takahama et al. | 422/98 |
| 4,441,981 | 4/1984 | Okamoto et al. | 204/426 |
| 4,482,635 | 11/1984 | Herskovitz et al. | 436/134 |
| 4,668,635 | 5/1987 | Forster | 436/134 |
| 4,718,992 | 1/1988 | Funahashi et al. | 204/153.1 |
| 5,063,164 | 11/1991 | Goldstein | 436/169 |

Primary Examiner—Robert J. Warden
Assistant Examiner—Robert Carpenter
Attorney, Agent, or Firm—Henry P. Sartorio

[57] ABSTRACT

A molybdenum, tungsten or vanadium salt-palladium, ruthenium or osmium salt solution for CO detection is made reversible by addition of ferric, chromium (VI) or cerium (IV) ion. The system is made more CO specific by adding an interference control salt which forms white or colorless precipitates with interfering species. The operational and shelf life are extended by a mixture of counterions; the acetate counterion is particularly useful.

16 Claims, 1 Drawing Sheet

SPECIFIC AND REVERSIBLE CARBON MONOXIDE SENSOR

RELATED APPLICATIONS

This application is a continuation in-part (CIP) of Ser. No. 08/009,066 filed Jan. 26, 1993.

BACKGROUND OF THE INVENTION

The invention relates generally to chemical sensors and more particularly to carbon monoxide sensors.

The reaction of Carbon Monoxide (CO) with a variety of molybdenum compounds was reported as early as 1910 [C. Zenghelis, Z. Anal. Chem, 40, 429, (1910)] and the literature was reviewed in 1935 by J. Schmidt, "Das Kohlenoxyd" Akad Verlag, Leipzig, p. 186, (1935). It is further presented in "Spot Tests in Inorganic Analysis" by F. Feigel, V. Anger, R. Oesper, Elsevier Publishing Company, New York, p. 168 (1972).

The three (3) basic equations for the palladium catalyzed reduction of molybdenum by carbon monoxide are:

$$Mo^{+6} + CO \rightarrow Mo^{+3} + CO_2 \quad (1)$$

$$Pd^{+2} + CO \rightarrow Pd^0 + CO_2 \quad (2)$$

$$Pd^0 + Mo^{+6} \rightarrow Pd^{+2} + Mo^{+3} \quad (3)$$

The reaction in Equation (1) is very slow and, therefore, a catalyst ($Pd^{+2}$) is used. The $Pd^{+2}$, even in very small quantities, adsorbs and simultaneously gets reduced by CO as shown in Equation (2). $Pd^0$, in turn, enters into the reaction, Equation (3), producing molybdenum blue. Thus, a slightly yellow solution is changed to a blue color with the intensity of the blue color being directly related to CO exposure. As presented in Equations (1), (2) and (3), the reaction is not reversible and, therefore, has limited application in sensor technology.

To make the system reversible, therefore, there must be a secondary reaction which converts $Mo^{+3}$ back to $Mo^{+6}$, i.e., an oxidizer must be present. A successful reversing agent must meet the following two important criteria: (a) the regeneration reaction should be fast, and (b) the regenerating agent itself should quickly revert back to the starting state for the next cycle.

A reversible CO sensor is shown by Shuler et al., U.S. Pat. No. 4,043,934 which has a Mo, W or V color forming agent, Pd catalyst and Cu, Ni or Fe reversing agent. The sensing reagent is deposited on an inert carrier which is hydrophilic or contains water or $OH^-$ groups, e.g. silica gel, alumina, polymeric alcohol, polyglycol, cellulose, glass wool and sponges.

M. K. Goldstein in U.S. Pat. No. 5,063,164 describes a biomimetic sensor for detecting the presence of airborne toxins, including CO. That patent suggests several possible chemical recipes for this type of sensor, but does not address the criteria or requirements for a successful reversible sensor; nor does it address the chemistry or mechanisms to make the CO sensor completely specific.

Goldstein shows a solid state CO sensor having five components: (1) palladium salt, (2) molybdenum and/or tungsten salt or acid salt, (3) copper salt, (4) cyclodextrin molecular encapsulant which encapsulates at least one but not all of the other components, and (5) chloride salt, all impregnated into a substrate. The Mo,W/Pd/Cu system is as in Shuler. The improvement is the encapsulant which extends sensor lifetime. An excess of chloride ions are also provided to extend lifetime.

Goldstein does not reveal (a) how fast the reverse reaction occurs, or (b) whether it can stand a drastic environment like 100% CO. Goldstein uses $Cu^{+2}$ salts as the reversing agent, $Cu^{+2}$ and $Cu^+$ ions are very stable at ambient atmospheric conditions. Therefore, the $Cu^{+2}/Cu^+$ pair does not fully meet the criteria of a successful reversing agent for a deadly toxic gas like CO.

SUMMARY OF THE INVENTION

Accordingly, it is an object of the invention to provide an improved CO sensor.

It is also an object of the invention to provide a reversible CO sensor.

It is another object of the invention to provide a specific CO sensor which eliminates interferences.

It is a further object of the invention to provide a CO sensor with extended lifetime.

The invention is a reversible CO sensor formed of an aqueous solution of (1) molybdenum, tungsten or vanadium salts or acid salts, (2) palladium, ruthenium or osmium salt, (3) iron, chromium or cerium salt. The palladium, ruthenium or osmium salt provides palladium (II), ruthenium (VIII) or osmium (VIII) ion as a catalyst. The iron, chromium or cerium salt provides ferric ion, chromium (VI) ion or cerium (IV) ion as a reversing agent. The solution further can include an interference suppressing agent which forms a white or colorless precipitate to eliminate interferences and increase specificity. The invention further includes a long-life CO sensor based on palladium or other catalyst with mixed counterions which act as a redox property modifier for the catalyst. The CO sensor is formed of an aqueous solution of (1) molybdenum, tungsten or vanadium salts or acid salts, (2) palladium, ruthenium or osmium salt, (3) Pd(II) or other catalyst redox controlling counterion producing salt, (4) $Fe^{+3}$, $Cr^{+6}$ or $Ce^{+4}$ ion as the reversing agent, and (5) sodium salts or other interference suppressing agents.

DETAILED DESCRIPTION OF THE PREFERRED EMBODIMENTS

Figure 1:
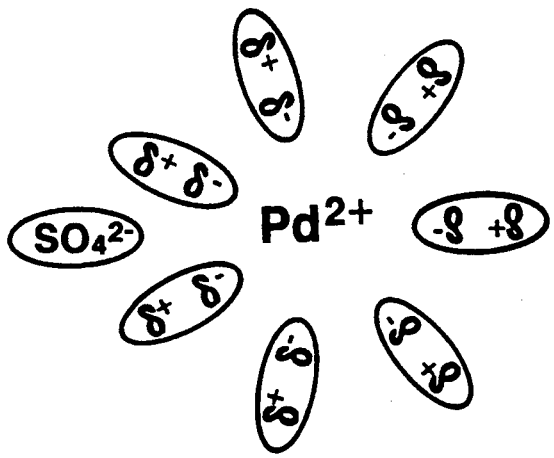
FIG. 1 is a diagram of a Pd(II) ion surrounded by water dipoles.

The CO sensing reagent according to the invention includes:

A. Color forming agent: Molybdenum ion is preferred; tungsten or vanadium can also be used.

B. Catalyst: Palladium is preferred; ruthenium and osmium are new catalysts according to the invention.

C. Reversing agent: Ferric ion is preferred and copper or nickel can also be used; chromium and cerium are new reversing agents according to the invention.

D. Redox property modifier: Acetic acid salts are preferred.

E. Interference suppressing agent: sodium ion is preferred for hydrogen sulfide interference.

Thus, the invention adds new agents, for redox property modification and/or interference suppression, to combinations of known indicators, catalysts and reversing agents. The invention also provides new catalysts and reversing agents. The preferred color forming agent is molybdenum as described herein. However, tungsten and vanadium are also known indicators for CO.

The preferred catalyst is palladium, Pd(II), as described herein. However, in accordance with the invention, ruthenium, Ru(VIII), and osmium, Os(VIII), can also be used for the catalyzed reduction of molybdenum by CO.

The choice of a reversing agent depends on its ability to produce the desired reactions only, and nothing more. The first requisite is that the $Mo^{+3}$ formed with the reaction of $Pd^{+2}$, CO and $Mo^{+6}$ goes back to $Mo^{+6}$ and no other valence states of the Mo. This requires a reversing compound whose redox potential closely matches that of $Mo^{+3}$ going to $Mo^{+6}$ so that the reaction proceeds spontaneously in the thermodynamic sense. The second requirement is that the selected oxidizing agent, when used, regenerates itself and not a series of compounds of various chemical formula and valence states. Based on these criteria, ferric ion is preferred (irrespective of the counter ion) as the reversing agent in the formulation of a CO sensing chemistry. The reverse reaction proceeds as follows:

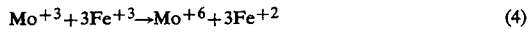
$$Mo^{+3} + 3Fe^{+3} \rightarrow Mo^{+6} + 3Fe^{+2} \qquad (4)$$

Eventually, by air oxidation $Fe^{+2}$ returns to $Fe^{+3}$ to be available for reuse.

Alternatively, chromium (VI) ion or cerium (IV) ion can be used as the reversing agent, or other reversing agents including copper or nickel.

The amount of ferric ion (such as ferric chloride), chromium (VI) ion or cerium (IV) ion used strictly depends on the dynamic range of concentrations of CO to be detected and the desired time delay for reversibility. In fact, if time is not a criterion, the reliance on oxygen in the air to cause the reversibility is perfectly acceptable.

The CO sensor chemistry is thus a solution of (1) molybdenum, tungsten or vanadium salts or acid salts which provides the $Mo^{+6}$, $W^{+6}$ or $V^{+5}$ ion, (2) palladium, ruthenium or osmium salt which provides the $Pd^{+2}$, $Ru^{+8}$ or $Os^{+8}$ ion, and (3) iron (ferric), chromium or cerium salt which provides the $Fe^{+3}$, $Cr^{+6}$ or $Ce^{+4}$ ion. The solution is typically aqueous, but other solvents might be used. The molybdenum acid/salt may be selected from molybdosilicic acid and salts thereof, molybdenum trioxide, heteropolyacids of molybdenum, ammonium molybdate, ammonium molybdophosphate, molybdophosphoric acid, organomolybdenum compounds, and alkali metal or alkaline earth metal salts of the molybdate anion. The tungsten acid/salt may be selected from tungstosilicic acid and salts thereof, tungsten trioxide, tungstophosphoric acid, organotungsten compounds, heteropolyacids of tungsten, ammonium tungstate, and alkali metal or alkaline earth metal salts of the tungstate ion. The vanadium salt may be selected from vanadium (V) oxide, vanadyl phthalocyanine, vanadium (V) trichloride oxide, vanadium (V) trifluoride oxide, vanadium triisopropoxy oxide, vanadyl octaethylporphine. The palladium salt may be selected from palladium sulfate, palladium sulfite, palladium pyrosulfite, palladium chloride, palladium bromide, palladium iodide, palladium perchlorate, palladium acetate, palladium oxalate, palladium citrate, palladium acetylacetone, allylpalladium bromide, $CaPdCl_4$, $Na_2PdCl_4$, $K_2PdCl_4$. The ruthenium and osmium salts include ruthenium (VIII) oxide and osmium (VIII) oxide. The iron (ferric) salt may be selected from ferric chloride, ferric sulfate, ferric bromide, ferric iodide, ferric perchlorate, ferric fluoride, ferric acetylacetonate, ferric ammonium citrate, ferric ammonium sulfate, ferric nitrate, ferric oxalate, ferric phosphate, ammonium ferric citrate, ammonium ferric oxalate. Chromium (VI) salts include but are not limited to potassium dichromate, ammonium dichromate, sodium dichromate, sodium chromate, potassium chromate. Cerium (IV) salts include but are not limited to cerium sulfate, ammonium cerium nitrate, ammonium cerium sulfate. All the salts must be soluble.

In operation, the $Mo^{+6}$ is reduced to $Mo^{+3}$ by the CO in the presence of the $Pd^{+2}$, $Ru^{+8}$ or $Os^{+8}$ catalyst. The $Fe^{+3}$, $Cr^{+6}$ or $Ce^{+4}$ then oxidizes the $Mo^{+3}$ back to $Mo^{+6}$. The $W^{+6}$ or $V^{+5}$ color forming agent behaves similarly.

For the detection of CO between 0 and 500 ppm, a typical chemical system consists of:

Palladium Sulfate (0.04 wt. %)
Molybdosilicic Acid (0.2 wt. %)
Ferric Chloride (0.04 wt. %)

in aqueous solution. This composition is modified for other dynamic ranges.

The second part of the requirement for a CO sensor is that it be specific. All existent CO sensors including the one defined in U.S. Pat. No. 5,063,164 suffer from a variety of interferences of which hydrogen sulfide is most common. For example, palladium sulfide, molybdenum sulfide and copper sulfide (which would be formed in U.S. Pat. No. 5,063,164) are all black/brown which prohibits measurement of the yellow to blue color change when $Mo^{+6}$ is reduced to $Mo^{+3}$. Iron sulfide, which is yellow/green can also cause some problems. The solution, therefore, is to add a fourth component to the system which not only preferentially forms a sulfide, but a white or colorless one which will not interfere with the CO measurement. To accomplish this, sodium chloride (2 wt. %) is incorporated into the system. The sodium ion is the interference suppressing agent.

The four (4) component chemical system was extensively tested with a UV/VIS spectrophotometer. The following table shows the results of these tests. This formulation for a CO sensor indicates no response to the key Occupational Safety and Health Administration (OSHA) interferences.

| INTERFERENCE LEVEL | RESPONSE | OSHA LEVEL |
|---|---|---|
| Propane (1000 ppm) | 0 | 1000 ppm |
| NO₂ (30 ppm) | 0 | 3 ppm |
| Butane (800 ppm) | 0 | 800 ppm |
| SO₂ (10 ppm) | 0 | 2 ppm |
| N₂O (100 ppm) | 0 | |
| H₂S (50 ppm) | 0 | 10 ppm |
| CO₂ (100%) | 0 | 10000 ppm |
| Methane (100%) | 0 | 1000 ppm |

Other salts which are sources of suitable ions can also be used to eliminate interferences and enhance specificity by producing white or colorless precipitates with the interfering species. These salts may be selected from salts of sodium, ammonium, lithium, potassium, calcium, magnesium, beryllium, aluminum, platinum, cobalt, with counterions nitrate, acetate, chloride, sulfate, phosphate, chlorate, nitrite, perchlorate, carbonate, bicarbonate.

The interference suppressing ion must preferentially form a precipitate with the interfering species instead of one of the components of the system forming a precipitate with the interfering species. The precipitate could also have a color if the color does not overlap the measurement wavelength or has a resolvable overlap.

Extending the shelf life and operational life of the CO sensor is very important. Doing so is difficult, and involves modification of the redox properties of the catalyst. This was achieved in the following way:

The catalyst is Palladium(II). When common salts of palladium ($PdSO_4$, $PdCl_2$, etc.) are dissolved in water, Pd(II) exists in the solvated form, as shown in FIG. 1. Water molecules form dipoles ($\delta^- \text{-} \delta^+$) which surround the Pd (II) ion. The sulfate counterion also present. The counterions are also similarly solvated.

In the aquo form, Pd(II) is energetically very prone to reduction. When $Pd^{+2}$ is surrounded by neutral molecules like water, ethanol, ethylene glycol, glycerol, and molecules having reducing functional groups, the operational and shelf life of the sensor chemistry are diminished drastically because of reduction without CO. Similar results occur with counterions like $SO_4^{-2}$, $Cl^-$, $PO_4^{-3}$, $HPO_4^{-2}$, etc. Because the species surrounding the $Pd^{+2}$ determines its redox properties, the properties of $Pd^{+2}$ can be controlled by carefully selecting its counterions, i.e., by including a redox property modifier.

Figure 2:
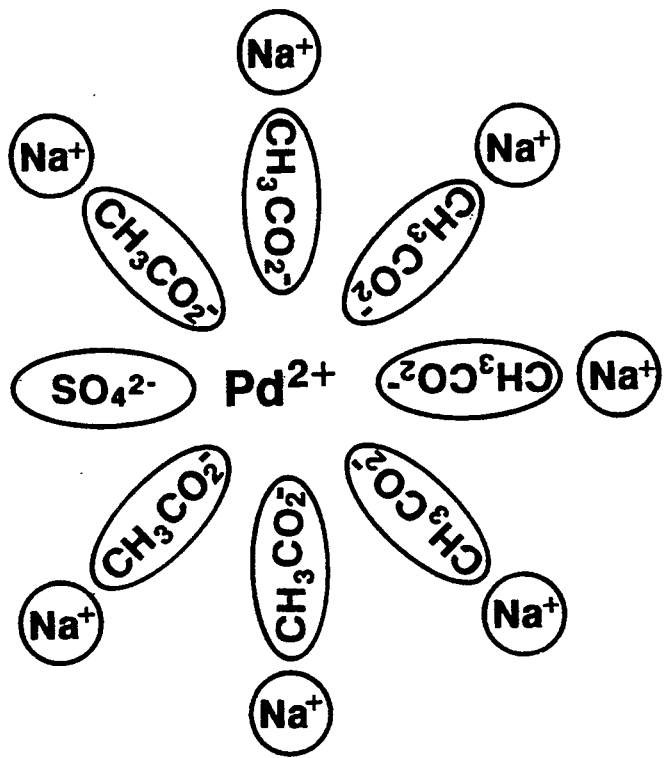
FIG. 2 is a diagram of a Pd(II) ion surrounded by sulfate and acetate counterions.

When neat CO is passed through a solution of $PdSO_4$ in pure water, the solution turns black immediately. However, when $PdSO_4$ is dissolved in sodium acetate saturated water, it takes fifteen times longer to get dark. The acetate ions ($CH_3CO_2^-$) now surround the Pd(II) ion as shown in FIG. 2. The sulfate counterion is also present. Thus, the presence of acetate counterion greatly influences the redox properties of $Pd^{+2}$. This difference between sulfate and acetate counterions is used to extend lifetime.

The invention includes a CO sensing chemistry based on palladium with mixed counterions. By carefully adjusting the proportion of acetate and sulfate, or acetate and chloride counterions, the redox properties of $Pd^{+2}$ are modulated, thereby prolonging the shelf life and operational life of the sensor.

Thus, the invention includes the addition of suitable counterions to the molybdenum/palladium combination. Ferric ion is added for reversibility and sodium salt for specificity as previously described. However, the bicounterion concept is applied to the palladium catalyst to achieve prolonged shelf life and operational life.

The redox property modifying counterion can be provided by the following: sodium acetate, potassium acetate, ammonium acetate, magnesium acetate, copper acetate, lithium acetate or other acetic acid salt. Other salts which prevent the reduction of the catalyst and subsequent color forming reaction in the absence of CO could also be used. The amount of counterion to be added is typically in the range of ten times the molar concentration of palladium.

Changes and modifications in the specifically described embodiments may be carried out without departing from the scope of the invention which is intended to be limited only by the scope of the appended claims.

We claim:

1. A CO sensor comprising, in solution:
   a color forming agent which is reduced by CO and produces a color change;
   a catalyst which is reduced by CO and which thereby also reduces the color forming agent;
   a reversing agent which oxidizes the reduced color forming agent back to its initial oxidation state;
   a redox property modifying agent which prevents reduction of the catalyst and the color forming agent in the absence of CO;
   wherein, the reversing agent is selected from the group consisting of a source of $Fe^{+3}$, $Cr^{+6}$ and $Ce^{+4}$ ions and the redox property modifying agent is a source of acetate counterions.

2. The CO sensor of claim 1 further comprising:
   an interference suppressing agent which forms noninterfering precipitates with interfering species to prevent the interfering species from forming precipitates with any of the color forming agent, catalyst, and reversing agent.

3. The CO sensor of claim 1 wherein the source of acetate counterions is an acetic acid salt selected from the group consisting of sodium acetate, ammonium acetate, potassium acetate, lithium acetate, magnesium acetate and copper acetate.

4. The CO sensor of claim 2 wherein the interference suppressing agent comprises a source of ions which form white or colorless precipitates with interfering species.

5. The CO sensor of claim 4 comprising a source of ions which produce white or colorless sulfides.

6. The CO sensor of claim 2 wherein the interference suppressing agent is a source selected from the group consisting of sodium, potassium, ammonium, calcium, lithium, magnesium and beryllium ions.

7. The CO sensor of claim 6 wherein the source of ions is selected from the group consisting of sodium, potassium, ammonium, lithium, beryllium, magnesium, and calcium salts; said salts having counterions selected from nitrate, acetate, chloride, sulfate, phosphate, chlorate, perchlorate, nitrite, carbonate, and bicarbonate.

8. The CO sensor of claim 7 wherein the salt is sodium chloride.

9. The CO sensor of claim 1 wherein
   the color forming agent is selected from the group consisting of a source of $Mo^{+6}$, $W^{+6}$ and $V^{+5}$ ions;
   the catalyst is selected from the group consisting of a source of $Pd^{+2}$, $Ru^{+8}$ and $Os^{+8}$ ions.

10. The CO sensor of claim 9 wherein
    the color forming agent is selected from the group consisting of molybdenum salts, molybdenum acid salts, molybdenum organometal complexes, tungsten salts, tungsten acid salts, tungsten organometal complexes, vanadium salts, and vanadium organometal complexes;
    the catalyst is selected from the group consisting of palladium salts, ruthenium salts, and osmium salts;
    the reversing agent is selected from the group consisting of iron salts, chromium salts, and osmium salts.

11. The CO sensor of claim 10 wherein
    the molybdenum salt or acid salt is selected from the group consisting of molybdosilicic acid and salts thereof, molybdenum trioxide, heteropolyacids of molybdenum, ammonium molybdate, ammonium molybdophosphate, molybdophosphoric acid, organomolybdenum compounds, and alkali metal or alkaline earth metal salts of the molybdate anion;

the tungsten salt or acid salt is selected from the group consisting of tungstosilicic acid and salts thereof, tungstophosphoric acid, organotungsten compounds, heteropolyacids of tungsten, tungsten trioxide, ammonium tungstate, and alkali metal or alkaline earth metal salts of the tungstate ion;

the vanadium salt or organometal complex is selected from the group consisting of vanadium (V) oxide, vanadyl phthalocyanine, vanadium (V) trichloride oxide, vanadium (V) trifluoride oxide, vanadium triisopropoxy oxide, vanadyl octaethylporphine;

the palladium salt is selected from the group consisting of palladium sulfate, palladium sulfite, palladium pyrosulfite, palladium chloride, palladium bromide, palladium iodide, palladium acetate, palladium perchlorate, $CaPdCl_4$, $Na_2PdCl_4$, $K_2PdCl_4$, palladium oxalate, palladium citrate, palladium acetylacetonate, allylpalladium bromide;

the ruthenium salt is ruthenium (VIII) oxide;

the osmium salt is osmium (VIII) oxide;

the iron salt is selected from the group consisting of ferric chloride, ferric sulfate, ferric bromide, ferric iodide, ferric perchlorate, ferric fluoride, ferric acetylacetonate, ferric ammonium sulfate, ferric nitrate, ferric oxalate, ferric phosphate, ammonium ferric citrate, ammonium ferric oxalate;

the chromium salt is selected from the group consisting of potassium dichromate, ammonium dichromate, sodium dichromate, sodium chromate, potassium chromate;

the cerium salt is selected from the group consisting of cerium sulfate, ammonium cerium nitrate, ammonium cerium sulfate.

12. A CO sensor comprising, in solution:
   a source of $Me^{+6}$, $W^{+6}$ or $V^{+5}$ ions;
   a source of $Pd^{+2}$, $Ru^{+8}$ or $Os^{+8}$ ions and first counterions;
   a source of $Fe^{+3}$, $Cr^{+6}$ or $Ce^{+4}$ ions;
   a source of second counterions to the $Pd^{+2}$, $Ru^{+8}$ or $Os^{+8}$ ions which substantially prevent the $Pd^{+2}$, $Ru^{+8}$ or $Os^{+8}$ ions from being reduced by the first counterions and other counterions in the solution, wherein the second counterions are acetate counterions.

13. The CO sensor of claim 12 wherein the ratio of second counterions to $Pd^{+2}$, $Ru^{+8}$ or $Os^{+8}$ ions is about 10:1.

14. The CO sensor of claim 12 wherein the source of second counterions is an acetic acid salt.

15. The CO sensor of claim 12 further comprising sodium chloride.

16. In a CO sensor having a $Mo_{+6}$, $W^{+6}$ or $V^{+5}$ color forming agent, catalyst, and reversing agent in solution, the improvement comprising:
   selecting the catalyst from $Ru^{+8}$ or $Os^{+8}$;
   selecting the reversing agent from $Cr^{+6}$ or $Ce^{+4}$.

* * * * *